United States Patent
Fix

(10) Patent No.: US 10,070,947 B2
(45) Date of Patent: Sep. 11, 2018

(54) LAB ANALOG FOR INSERTION INTO A CAVITY OF A PRINTED MODEL

(71) Applicant: Medentika GmbH, Hügelsheim (DE)

(72) Inventor: Frank Fix, Remchingen (DE)

(73) Assignee: Medentika GmbH, Hugelsheim (DE)

( * ) Notice: Subject to any disclaimer, the term of this patent is extended or adjusted under 35 U.S.C. 154(b) by 137 days.

(21) Appl. No.: 15/063,277

(22) Filed: Mar. 7, 2016

(65) Prior Publication Data

US 2016/0262858 A1   Sep. 15, 2016

(30) Foreign Application Priority Data

Mar. 9, 2015   (EP) .................................... 15158227

(51) Int. Cl.
*A61C 13/34*   (2006.01)
*A61C 8/00*   (2006.01)
*A61C 13/00*   (2006.01)

(52) U.S. Cl.
CPC ............ *A61C 13/34* (2013.01); *A61C 8/0001* (2013.01); *A61C 13/0019* (2013.01)

(58) Field of Classification Search
CPC ... A61C 13/34; A61C 8/0001; A61C 13/0019; A61C 8/00
See application file for complete search history.

(56) References Cited

U.S. PATENT DOCUMENTS

| | | | | |
|---|---|---|---|---|
| 4,054,995 A | * | 10/1977 | Yoshida | A61C 9/002 433/74 |
| 5,658,147 A | * | 8/1997 | Phimmasone | A61C 8/0001 433/173 |
| 5,871,358 A | | 2/1999 | Ingber et al. | |
| 6,227,856 B1 | | 5/2001 | Beaty et al. | |
| 6,540,516 B1 | * | 4/2003 | Ziegler | A61C 8/0001 433/214 |
| 7,344,376 B2 | * | 3/2008 | Beaty | A61C 8/0001 433/173 |
| 8,790,408 B2 | * | 7/2014 | Marotta | A61B 19/50 623/17.19 |
| 9,414,898 B2 | * | 8/2016 | Bederak | A61C 13/34 |
| 2003/0162148 A1 | | 8/2003 | Prestipino | |
| 2009/0104585 A1 | * | 4/2009 | Diangelo | A61C 8/0001 433/223 |

(Continued)

FOREIGN PATENT DOCUMENTS

DE    102013004175 A1    9/2014

OTHER PUBLICATIONS

European Search Report and Written Opinion for EP15158227.7 dated Apr. 28, 2015, 8 pages.

*Primary Examiner* — Nicholas Lucchesi
(74) *Attorney, Agent, or Firm* — Foley & Lardner LLP

(57) ABSTRACT

A lab analog for insertion into a cavity of a printed model and for accommodating an abutment comprises an essentially cylindrical base body that extends along a longitudinal axis, a first centering section for centering the lab analog in the cavity of the printed model, the first centering section adjoining the base body in the coronal direction, a second centering section for centering the lab analog in the cavity of the printed model, the second centering section adjoining the base body in the apical direction, restraining elements for restraining the lab analog in the longitudinal direction, and at least one fixing element to fix the lab analog against rotation.

17 Claims, 11 Drawing Sheets

(56) References Cited

U.S. PATENT DOCUMENTS

2015/0045925 A1   2/2015  Powell et al.
2016/0250008 A1*  9/2016  Brun ................... A61C 8/0001
                                                            433/213

* cited by examiner

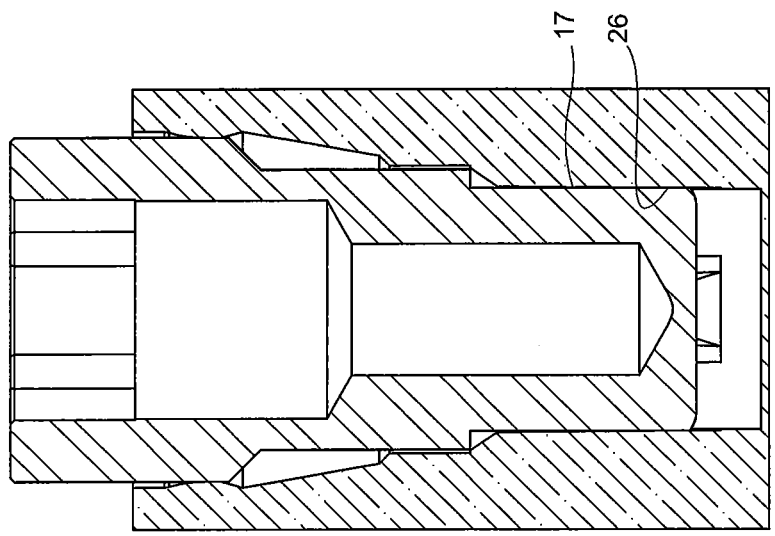
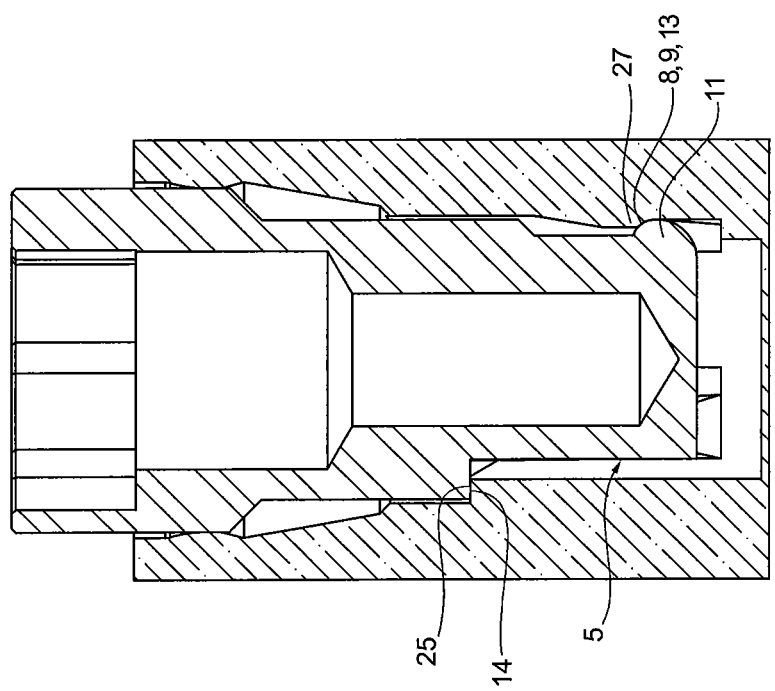
Fig. 10b
Fig. 10c

LAB ANALOG FOR INSERTION INTO A CAVITY OF A PRINTED MODEL

CROSS REFERENCE TO RELATED APPLICATION

This application claims the priority benefit of the EP Patent Application Number 15158227.7, filed on Mar. 9, 2015, entitled "Lab analog for insertion into a cavity of a printed model," which is hereby incorporated by reference to the maximum extent allowable by law."

BACKGROUND

The present invention relates to a lab analog for insertion into a cavity in a printed model and for accommodating an abutment.

Lab analogs of this type are used, for example, in modeling prosthetic tooth restorations which are fixed in the jaw of a patient with the aid of implants.

It is known to scan teeth in three dimensions with the aid of digital scanners. The data obtained are used to produce so-called printed models (impressions) using 3D printers. If a prosthetic tooth restoration that is supported by implants is to be individually prepared for a patient, a "scan body" is screwed into an implant which is anchored in the jaw of a patient. The scan body is, for example, shaped like a post with one or more flat surfaces and is recognized when the teeth are scanned. It reproduces the exact orientation of the implant and thus serves for subsequent exact positioning of an abutment in (on the) printed model. The prosthetic tooth is then modeled onto the abutment in the printed model and later screwed into the implant in the patient's jaw together with the abutment.

In order to be able to connect the printed model with the abutment, lab analogs are provided in the printed model that, like the actual implant in the jaw of the patient, comprise appropriate platforms for the selected abutments. In order to be able to anchor the lab analog in the printed model, a cavity is provided into which the lab analog is subsequently inserted. The cavity is stored in the digital data set and when the printed model is printed, it is directly generated. The configuration of the cavity and its position are selected in dependence of the scan body and the shape of the corresponding lab analog.

Because of the manufacturing tolerances during generation of the printed model and tolerances during generation of the abutment, exact positioning of the abutment in the printed model is very difficult. Modeling the prosthetic tooth on the abutment so that it subsequently fits seamlessly into the teeth of the patient is thus extremely difficult.

SUMMARY

In view of the problems described above, the object of the present invention is to provide an improved lab analog for insertion into a cavity of a printed model, a printed model with a corresponding cavity and the resulting system comprising the lab analog and the printed model, which enable an abutment to be precisely positioned in the printed model.

The object is achieved by means of a lab analog with the features of claim 1, a printed model with the features of claim 12 and a system with the features of claim 16.

In accordance with the invention, the lab analog comprises an essentially cylindrical base body which extends along a longitudinal axis, a first centering section and a second centering section. The first centering section adjoins the base body in the coronal direction, while the second centering section adjoins the base body in the apical direction. The two separated centering sections render it possible that the lab analog can be centered precisely in the cavity of the printed model. In particular, tipping of the lab analog relative to the cavity is prevented.

Furthermore, the lab analog comprises restraining elements to restrain the lab analog in the longitudinal direction and at least one fixing element to fix the lab analog against rotation. Movement of the lab analog in the longitudinal direction is prevented with the aid of the restraining elements. In addition, the lab analog is fixed in rotational direction around the longitudinal axis of the base body by means of the fixing elements.

Together, the two centering sections, the restraining elements and the fixing element completely fix the lab analog in the cavity, so that it no longer has any degrees of freedom. Movement of the lab analog in the cavity is thus prevented.

In accordance with the invention, the first centering section is provided with a centering surface. The second centering section comprises at least one centering element. Both the centering surface and the centering element widen the cavity radially during insertion of the lab analog.

Widening occurs in the elastic region of the printed model. The material for manufacturing the printed model will have been selected appropriately. Preferably, the printed model consists of a plastic, preferably a thermoplastic or light-curing plastic.

Preferably, the centering element is configured as an apical centering surface, wherein the lab analog comprises at least one apical centering surface. It is also possible for the lab analog to comprise a plurality of centering surfaces, for example two, three, four, five, six, eight, 10, 12 or more than 12. In the context of the present invention, it has been observed that the precision with which the lab analog can be centered in the cavity rises with an increasing number of centering surfaces. In practice, two to four centering surfaces have been shown to be sufficient.

A first restraining element is configured as a bead and a second restraining element is configured as a step. The bead, which is preferably disposed in the apical region of the lab analog, engages behind a projection in the cavity in the insertion direction when the lab analog is inserted, in a manner such that the step becomes seated at a shoulder in the cavity. Because it engages behind the projection, the step of the lab analog is pulled in the direction of the shoulder of the cavity until it becomes seated at the shoulder. Preferably, the bead is disposed perpendicular to the longitudinal direction of the base body and runs in the circumferential direction of the base body. Optionally, it comprises a lateral surface that is rounded in the insertion direction, which has an asymmetrical profile in cross-section. Preferably, the sectional plane of the cross-section is along the longitudinal axis of the base body. The lateral surface forms a cross-sectional edge that has a smaller radius along a coronally disposed region than along an apically disposed region. The formulation "along a coronally/apically disposed region" in this context means that the radius of the cross-sectional edge, i.e. of the lateral surface, remains the same over the coronally/apically disposed region and in particular is constant. In the apical region, the lateral surface perpendicular to the longitudinal axis preferably runs closer to the longitudinal axis than in the coronal region.

In order to move the bead past the projection when inserting the lab analog into the cavity, the apical region of the lateral surface runs up to the projection, whereupon the latter is radially widened. After the bead has passed the projection in the region of its largest radial extension, the lateral surface slides along its coronal region away from the projection, whereupon the projection reverts to its original shape elastically. By means of this reversion, the projection pushes the bead and thus the lab analog along with it into the cavity.

Preferably, the projection has not reverted completely to its original shape and/or the lateral surface along its coronal region has not yet completely slid past the projection when the step becomes seated against the shoulder of the cavity. In this manner, the lab analog is pushed further into the cavity, but is blocked by the step becoming seated at the shoulder. Thus, the lab analog is restrained in the cavity.

In the context of the present invention, it has been discovered that the size of the radius of the apical region of the lateral surface has an influence on the insertion force when inserting the lab analog into the cavity. In this regard, a larger radius results in smaller insertion forces, whereas a smaller radius is associated with higher insertion forces. Preferably, the radius in the apical region is 0.4 mm to 0.6 mm, particularly preferably 0.5 mm. It has also been discovered that the size of the radius along the coronal region of the lateral surface significantly influences the withdrawal force which has to be overcome in order to remove the lab analog from the cavity. Preferably, the radius along the coronal region of the lateral surface is 0.2 mm to 0.4 mm, particularly preferably 0.3 mm.

When dimensioning the bead, particular attention was paid to the fact that the projection in the cavity is not damaged or even squashed by being deformed. To this end, a radius which remains the same and in particular is constant in the apical region of the lateral surface is used so that the projection is widened in a uniform manner. The same is true for the coronal region of the lateral surface. Preferably, the projection is deformed elastically when inserting or removing the lab analog, particularly preferably exclusively elastically.

Optionally, the step becomes seated on the shoulder in such a manner that, when inserting the lab analog into the cavity, a user receives an acoustic and/or haptic feedback signal. Such an acoustic feedback signal may, for example, be a click which occurs when the step engages fully with the shoulder. This ensures that the lab analog is sitting correctly in the cavity.

The fixing element is flat in construction and sits flush against the printed model when the lab analog has been inserted. Preferably, the fixing element becomes seated against a corresponding flat counterpart in the cavity. Optionally, the measurements of the fixing element and its counterpart are such that almost the whole of the two surfaces are seated against each other and thus fix the lab analog against rotation. Preferably, the fixing element is formed as a fixing surface, wherein the lab analog comprises at least one fixing surface. However, it is also conceivable that the lab analog comprises a plurality of fixing surfaces, for example two, four, six, eight, 10, 12 or more than 12.

In the context of the present invention, the term "printed model" means an impression which has been produced using a 3D printing method or by means of shaping. The terms "printed model" and "impression" are used synonymously.

In a preferred embodiment, the centering section comprises a centering chamfer which adjoins the coronal centering surface in the coronal direction, wherein the first centering section has a larger diameter compared with the base body. The centering chamfer is preferably at an angle to the longitudinal axis of the base body in the range 2 to 89 degrees, preferably 5 to 50 degrees, particularly preferably 10 to 45 degrees. The centering chamfer makes widening of the cavity to the diameter of the first centering section easier when inserting the lab analog. Because of the elastic extension of the cavity, the lab analog is firmly held by the printed model and is fixed completely securely in position by radial pressure. Optionally, the full circumference of the centering surface becomes seated on the cavity.

More preferably, at least one bead is disposed at the apical end of the second centering section and runs at least partially in the circumferential direction of the base body. Optionally, the bead is disposed in front of the step in the insertion direction of the lab analog.

Advantageously, at least one step is disposed at the apical end of the base body. Preferably, the lateral surfaces of the bead at which the bead engages behind the projection in the cavity, and a step surface with which the step becomes seated at the shoulder are disposed facing each other in the insertion direction of the lab analog.

Optionally, the lab analog comprises two mutually opposite centering elements or three centering elements disposed in the circumferential direction of the base body, which are configured as apical centering surfaces. Having two mutually opposite centering elements or three centering elements disposed in the circumferential direction ensures that the lab analog is at a uniform and constant distance in the circumferential direction from the inner wall of the cavity. In the region of the lower centering section, the lab analog is centrally disposed in the cavity of the printed model. Preferably, the three centering elements are uniformly disposed, i.e. are at the same angular positions in the circumferential direction.

Further preferably, the lab analog has four restraining elements, wherein two restraining elements are formed as beads and two restraining elements are formed as steps. The beads and steps are respectively disposed opposite one another. In this manner, the lab analog is restrained uniformly in the cavity. Preferably, the lab analog is concentrically restrained with respect to the cavity.

In a further embodiment, the steps and beads are offset by 90 degrees in the circumferential direction of the base body. In this manner, insertion of the lab analog into the cavity is made as easy as possible. The beads only have to be guided along the corresponding projections. They do not come into contact with the shoulders on which the steps become seated. Preferably, the radial extent of the bead is perpendicular to the longitudinal direction of the base body, approximately corresponding to the radius of the base body.

Further preferably, the lab analog comprises six restraining elements, wherein three restraining elements are formed as beads and three restraining elements are formed as steps. The beads and steps are preferably respectively uniformly distributed in the circumferential direction of the base body. The higher the number of restraining elements, the more evenly the lab analog is fixed in the longitudinal direction of the cavity.

Optionally, the apical centering surfaces are configured as lateral surfaces of the beads. In this manner, two functions are carried out, namely the centering function of the lower centering section and engaging behind a projection in the cavity are carried out by one and the same component, namely the bead. This saves on material and space. It should be understood that in this case, the number of centering surfaces corresponds to the number of beads.

More preferably, the fixing elements comprise two mutually parallel fixing surfaces or three fixing surfaces disposed in the circumferential direction of the base body which are each disposed parallel to the longitudinal axis of the base body and which confine the beads on the circumferential side (in the circumferential direction). Optionally, the fixing surfaces run to the apical end of the second centering section. In the coronal direction, the profile of the fixing surfaces is confined by the steps. Preferably, the number of fixing surfaces corresponds to the number of beads. Optionally, the dimension of the fixing surfaces is such that they sit as flush as possible with their corresponding counterparts in the cavity of the printed model. Preferably, an interference fit is formed between the fixing surfaces and their counterparts.

The present invention also encompasses a printed model with a cavity essentially configured as a bore in order to accommodate a lab analog, wherein the bore has an inner wall. The inner wall is provided with an introduction section to introduce the lab analog, which extends apically from a coronal opening of the bore. A radial tapering for centering the lab analog is disposed in the introduction section. When the lab analog has been inserted, the coronal centering surface of the first centering section becomes seated at the radial tapering. In particular, the printed model is configured such that it can accommodate the lab analog described above and preferably fix it securely.

The inner wall also comprises a shoulder for limiting the depth to which the lab analog is introduced, which shoulder adjoins the introduction section in the longitudinal direction of the bore. At least one seating surface for fixing the lab analog against rotation extends apically from the shoulder in the longitudinal direction. Optionally, the number of seating surfaces corresponds to the number of fixing surfaces for the lab analog or a multiple thereof, preferably two. The inner wall furthermore forms a projection which tapers the bore radially and a bead of the lab analog can be engaged behind it in the insertion direction in a manner such that a step of the lab analog becomes seated against the shoulder.

The introduction section, the shoulder, the seating surface and the projection fix a lab analog completely in the cavity, i.e. with no more degrees of freedom.

In the context of the present invention, the terms "introduce" and "insert" are used synonymously.

Preferably, the radial tapering in the introduction section is completely circumferentially disposed. This means that the apical centering surfaces of the lab analog can be completely circumferentially seated at the tapering. In this manner, the lab analog is centered as fully as possible in the region of the first centering section. Clearly, a sectional seat of the centering surfaces is sufficient in some cases.

In a preferred embodiment, four or six seating surfaces are disposed in pairs and parallel to each other, for example, and extend up to the projection. However, more than six seating surfaces may also be provided, for example. Optionally, the seating surfaces have a minimum dimension such that they are seated as flush as possible at the fixing surfaces of the lab analog. It is also conceivable for the seating surfaces to run conically in the insertion direction of the lab analog. In this manner, the fixing surfaces of the lab analog are almost completely flush against the seating surfaces of the cavity.

Advantageously, two of the seating surfaces are disposed in one plane, preferably parallel to the longitudinal direction of the bore. Optionally, the seating surfaces are positioned within a plane in a manner such that they become seated as closely as possible to the edges of the fixing surfaces that run laterally in the longitudinal direction of the lab analog. This ensures precise rotational fixing of the lab analog in the cavity.

The object of the invention is also achieved by means of a system in accordance with the present invention that comprises a printed model with a cavity and a corresponding lab analog. The system allows for very precise positioning of the lab analog in the cavity with a negligible play, or at least with tolerances that can be ignored in practice and which, when the abutment is subsequently installed in the mouth, do not cause any noticeable disadvantageous discrepancies. In this manner, an abutment that can optionally be screwed into the lab analog can be positioned exactly in the printed model. The position of the abutment in the printed model and in the actual dentition of the patient agree almost precisely. It is thus made sure that the prosthetic tooth constructed on the abutment with the help of the printed model can subsequently be inserted seamlessly, i.e. fittingly and without noticeable discrepancies, into the patient's dentition.

DESCRIPTION OF THE DRAWINGS

Two embodiments of the invention will now be described with the aid of the accompanying drawings, which show:

FIG. 10b the system in accordance with a second embodiment along the line of section F-F;

FIG. 10c the system in accordance with a second embodiment along the line of section G-G.

DETAILED DESCRIPTION

Figure 1B:
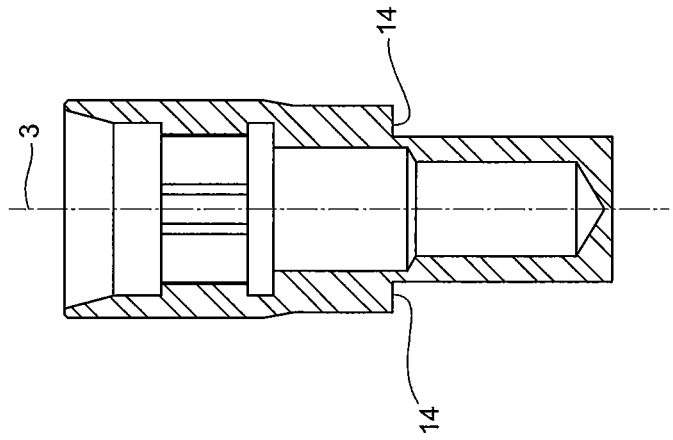
FIG. 1b a sectional view of the lab analog along the line of section A-A.
Figure 1A:
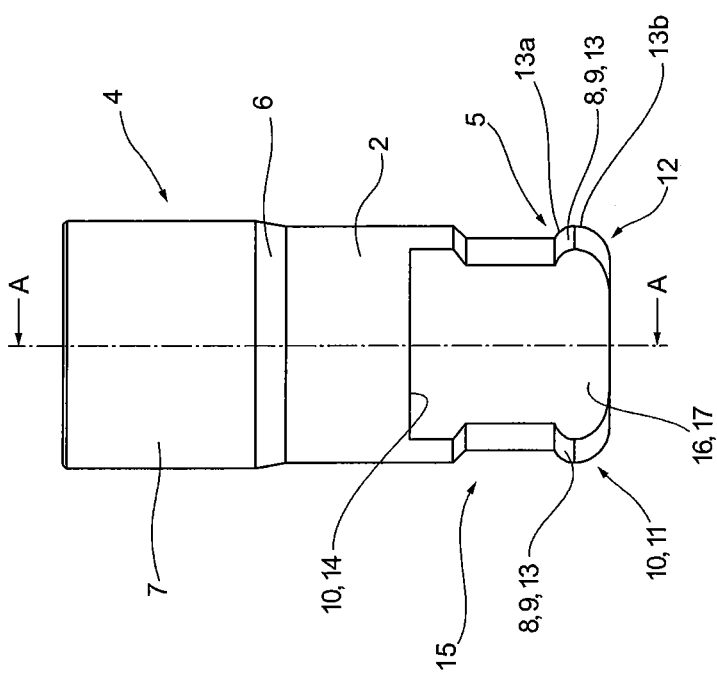
FIG. 1a a side view of a lab analog with the line of section A-A.
Figure 2:
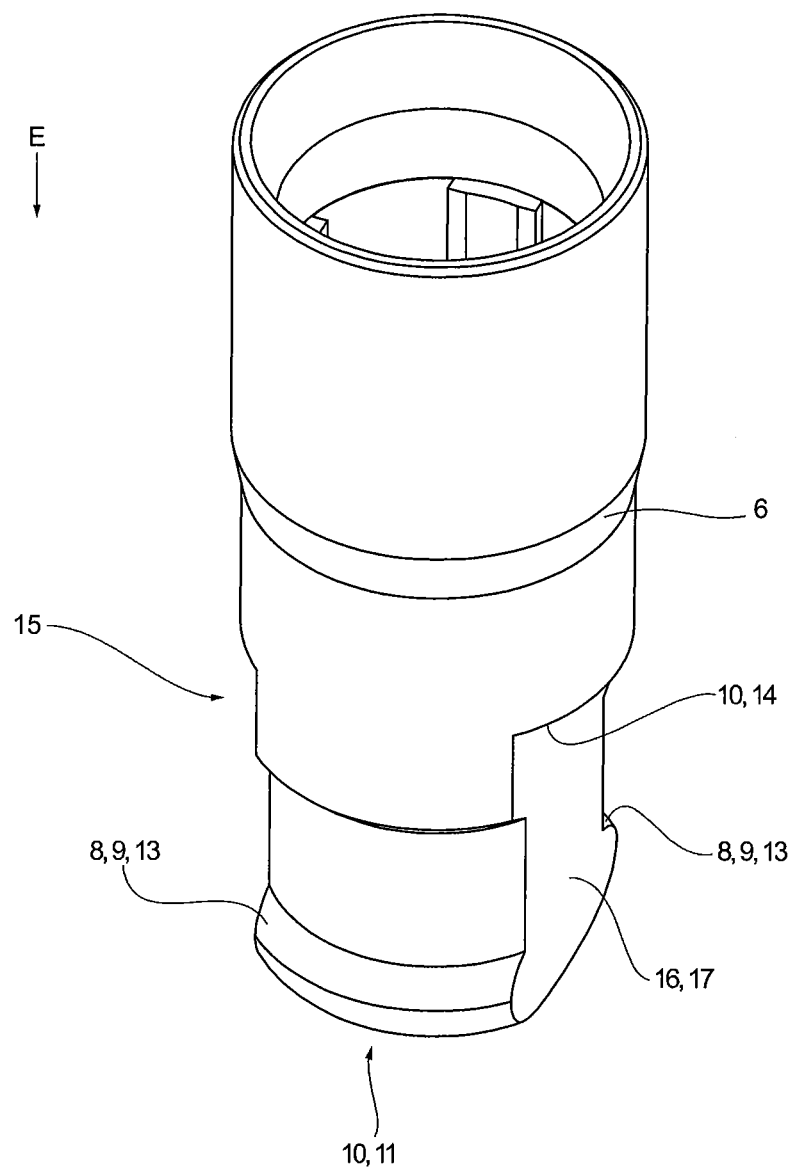
FIG. 2 a perspective view of the lab analog of FIG. 1.
Figure 3:
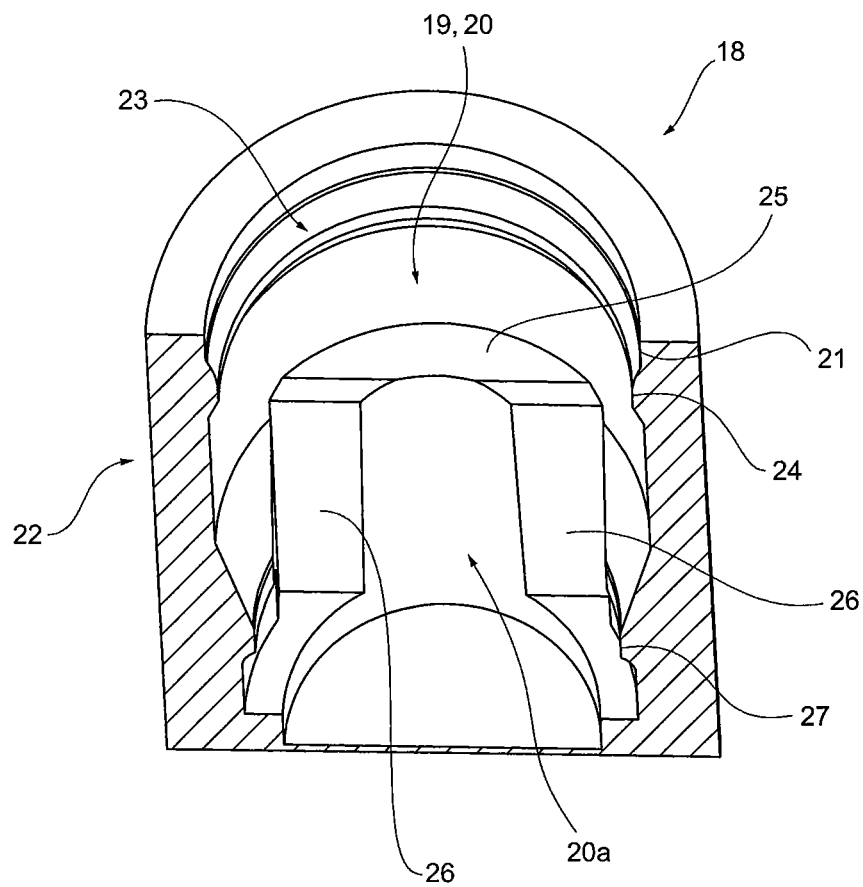
FIG. 3 a cavity of a printed model in sectional view.

FIGS. 1a, 1b and 2 show a lab analog 1 for insertion into a cavity of a printed model as shown in FIG. 3 and for accommodation of an abutment (not shown). The lab analog and the corresponding printed model together form a system in which they cooperate. This system is shown in FIGS. 4 to 6.

The lab analog 1 comprises an essentially cylindrical base body 2, which extends along a longitudinal axis. The base body 2 adjoins a first centering section 4 in the coronal direction and a second centering section 5 in the apical direction. The centering sections 4, 5 serve to center the lab analog in the cavity of the printed model.

The first centering section 4 is essentially cylindrical in shape. It has a central chamfer 6 which adjoins a coronal centering surface 7 in the coronal direction. The first centering section 4 has a larger diameter compared with the base body 2.

The second centering section 5 comprises two mutually opposite centering elements 8 which are formed as apical centering surfaces 9. Both the coronal centering surface 7 and the apical centering surfaces 9 serve to widen the cavity radially when the lab analog 1 is inserted.

The lab analog 1 also comprises four restraining elements 10 to restrain the lab analog 1 in the longitudinal direction. Two of the restraining elements 10 are formed as beads 11 which are mutually oppositely disposed at the apical end 12 of the second centering section 5. They run at least partially in the circumferential direction of the base body 2. The beads 11 have lateral surfaces 13 rounded in the insertion direction of the lab analog 1 that form the apical centering surfaces 9. The lateral surfaces 13 have a coronal region 13a (the so-called coronal lateral surface) and an apical region 13b (the so-called apical lateral surface) which—preferably seamlessly—adjoins the coronal lateral surface 13a. The radii of the coronal lateral surface 13a and the apical lateral surface 13b are different. Preferably, the lateral surface 13 has a larger radius in the apical region 13b than in the coronal region 13a; particularly preferably, the radius is 1.5 times larger, highly preferably two times larger, even more preferably 3 times larger.

The remaining two restraining elements 10 are formed as steps 14 that are disposed on the apical end 15 of the base body 2. The steps 14, too, are opposite to each other. Furthermore, the steps 14 are offset by 90 degrees with respect to the beads 11 in the circumferential direction of the base body.

The lab analog 1 also comprises two fixing elements 16 which are flat in construction and sit flush against the printed model when the lab analog 1 has been inserted. They act to fix the lab analog in the printed model against rotation. The fixing elements 16 have two mutually parallel, flat fixing surfaces 17 which are each disposed parallel to the longitudinal axis 3 of the base body 2 and which limit the beads 11 at the circumference.

Inside the lab analog 1 is a recess 23. An abutment into which a prosthetic tooth will be modeled can be inserted into and fixed in this recess 23.

FIG. 3 shows a portion of a printed model 18 (impression) with a cavity 19 in sectional view. The cavity 19 is formed as a bore 20 with an inner wall 21. It should be understood that the bore 20 may be formed as a blind bore with or without an opening in the base, or as a through bore. To illustrate it better, the outer boundary of the printed model 18 has been shown as being round. It should be understood that FIG. 3 only shows a section of the printed model 18.

The inner wall 21 forms an introduction section 22 for introducing the lab analog 1, which section extends apically from a coronal opening 23 of the bore 20. The introduction section 22 comprises a radial tapering 24 which serves to center the (corresponding) lab analog 1. The tapering 24 in the introduction section 22 is circumferential.

The inner wall 21 also forms a shoulder 25 to limit the depth to which the lab analog is introduced. The shoulder 25 adjoins the introduction section 22 in the longitudinal direction of the bore 20. Starting from the shoulder 25, a second inner bore 20a extends in the apical direction which is disposed concentrically with the bore 20 and has a smaller diameter compared with the bore 20.

The inner wall 21 comprises four seating surfaces 26 to fix the lab analog 1 against rotation, the surfaces extending from the shoulder 25 in the apical direction. The seating surfaces 26 are disposed parallel to each other, wherein two of the seating surfaces 26 lie in a plane that runs parallel to the longitudinal direction of the bore. The seating surfaces 26 are delimited in their width (transversely to the longitudinal direction of the bore 20) by the inner bore 20a. The size of the width is determined by the diameter of the inner bore 20a; thus, it is dependent on the radius of the inner bore 20a.

It should be understood that if the radius of the inner bore 20a is small, the width of the two seating surfaces 26 may be so great that the two seating surfaces 26 impinge against each other and combine to form a single surface. In the context of the invention, it has been discovered that the friction on inserting the lab analog 1 into the cavity 19 is substantially determined by the size of the individual seating surfaces 26, in particular their width. Thus if, for example, the inner wall 21 has four seating surfaces 26, then the friction upon insertion of the lab analog 1 is less than if two of the seating surfaces 26 were combined to form one overall seating surface and thus would be correspondingly wider. It has been shown to be advantageous if the distance between the two seating surfaces 26 in one plane corresponds to 1.5 times, preferably two times the width of a seating surface 26.

The sectional representation of FIG. 3 shows only two of the four seating surfaces 26. The bore 20 is symmetrical to the sectional plane.

Two projections 27 from the inner wall 21 taper the bore 20 radially. They are arcuate in shape, both in the circumferential direction and in the radial direction of the bore 20, wherein the arcs respectively and preferably follow the circumferential profile of the beads 11 in the circumferential direction and follow the profile of the lateral surfaces 13 of the beads 11 in the radial direction. A bead 11 of the lab analog 1 can thus engage behind the projections 27 in the introduction direction in a manner such that a step 14 of the lab analog 1 becomes seated at the shoulder 25. Because of the arcuate construction of the projections 27, nearly the entire surfaces of the apical centering surfaces 9 of the second centering section 5 become seated on the projections 27.

FIGS. 4a to 6b illustrate a system 28 which comprises the lab analog 1 from FIGS. 1a to 3 and a portion of the printed model 18 from FIG. 3 with the bore 20. The lab analog 1 is inserted in the bore 20.

It is shown that the first centering section 4 with the coronal centering surface 7 sits against the radial tapering 24 in the introduction section 22 of the bore 20. In this manner, the lab analog 1 is centered in the bore 20 in the region of the first centering section.

In the region of the second centering section 5 as well, the apical centering surfaces 9 sit against the projections 27 of the inner wall 21 and thus center the lab analog 1 in the bore 20.

When the lab analog 1 is inserted in the bore 20, the bore 20 is widened radially in the region of the radial tapering 24 by the centering chamfer 6 and the coronal centering surface 7 as well as in the region of the projections 27 by means of the beads 11.

Figure 4B:
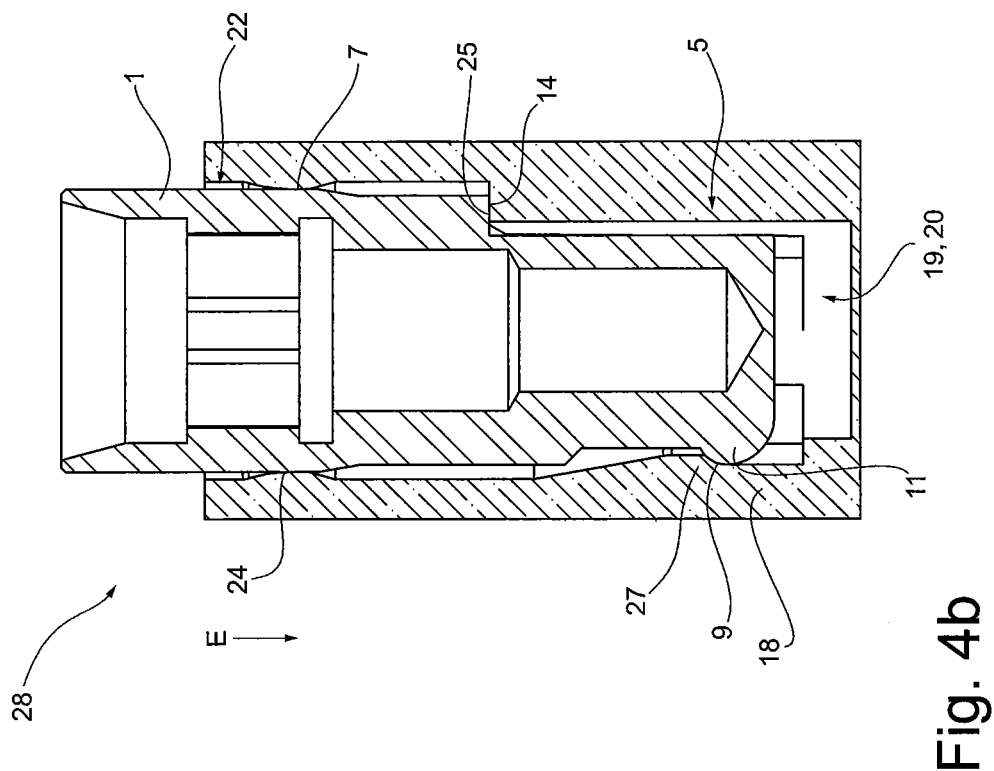
FIG. 4b a sectional view of the system along the line B-B.
Figure 4A:
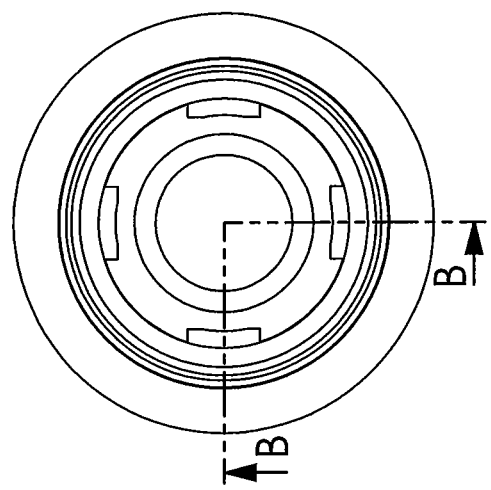
FIG. 4a a top view of a system with the line of section B-B.

Furthermore, FIG. 4b shows that the bead 11 of the inserted lab analog 1 engages behind the projection 27 of the bore 20 in the insertion direction E in such a manner that the step 14 of the lab analog 1 becomes seated on the shoulder 25 of the bore 20. In this manner, the lab analog 1 is restrained in the bore 20 in the longitudinal direction.

While the projections 27 cooperate with the beads 11 in such a manner that the beads 11 and thus the lab analog 1 are pushed in the apical direction (insertion direction E), the action of the force is limited by the steps 14 on the shoulders 25. In this manner, movement of the lab analog 1 in the apical and coronal direction is prevented.

Because FIG. 4b is a sectional representation, the second bead 11 as well as the second step 14 on the respective opposite sides are not shown. It is shown in FIG. 6b is that two projections 27 engage behind the two opposing beads 11. Two mutually opposing steps 14, which become seated on the shoulder 25 of the bore 20, can be seen in FIG. 5b. The sections of FIGS. 6b and 5b are at 90° to each other.

Figure 5B:
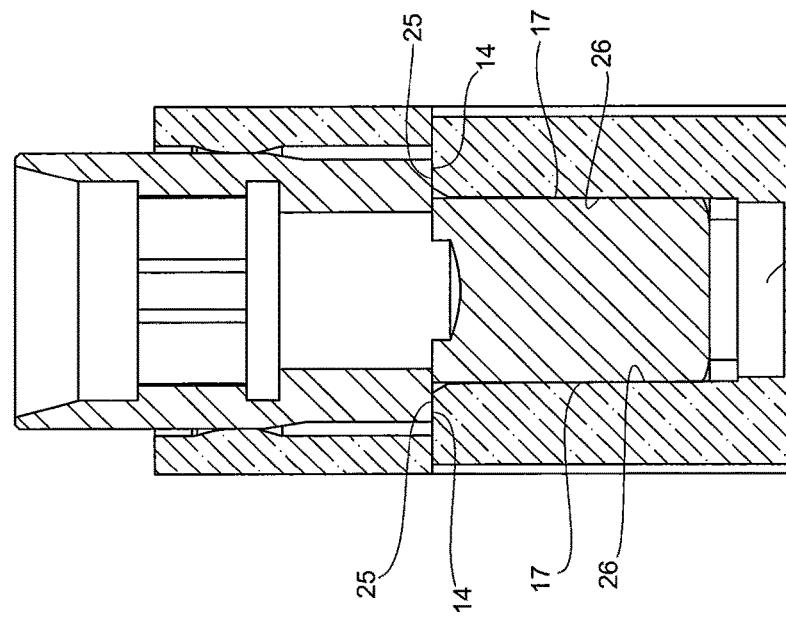
FIG. 5b the system along the line of section C-C.
Figure 5A:
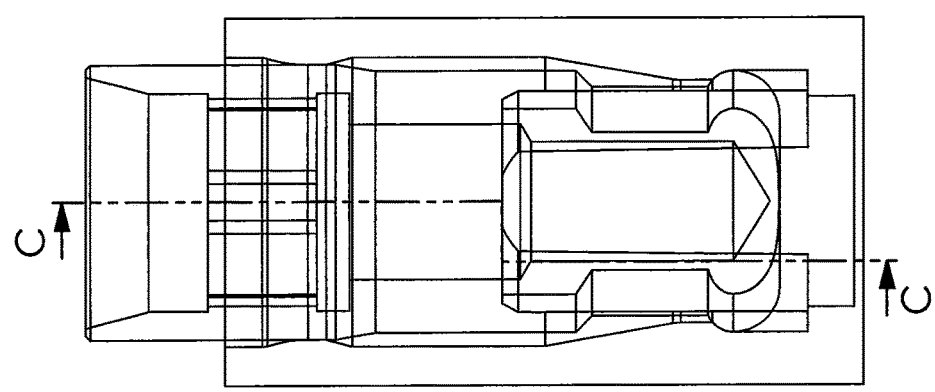
FIG. 5a a side view of the system with the line of section C-C.
Figure 6B:
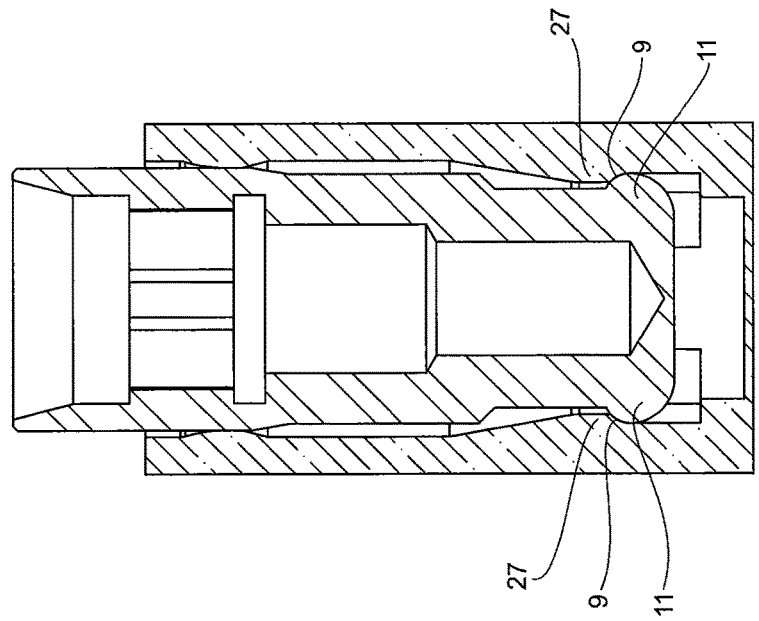
FIG. 6b the system along the line of section D-D.
Figure 6A:
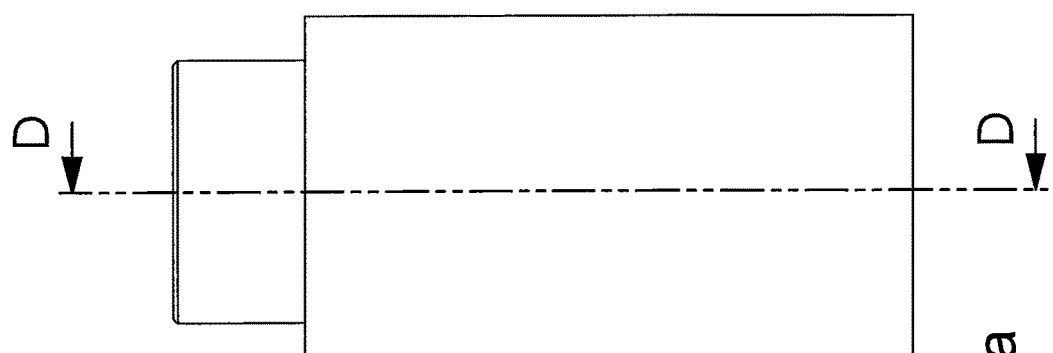
FIG. 6a a side view of the system with a line of section D-D.

In particular, FIG. 5b shows the seating of two fixing surfaces 17 of the lab analog 1 at two seating surfaces 26 of the bore 20. Preferably, the seating surfaces 26 are conically disposed in the insertion direction of the lab analog 1 so that the seat for the flat fixing surfaces 17 on the seating surfaces 26, which are also flat, is as large as possible. In this manner, the lab analog 1 is fixed against rotation in the bore 20.

Figure 7B:
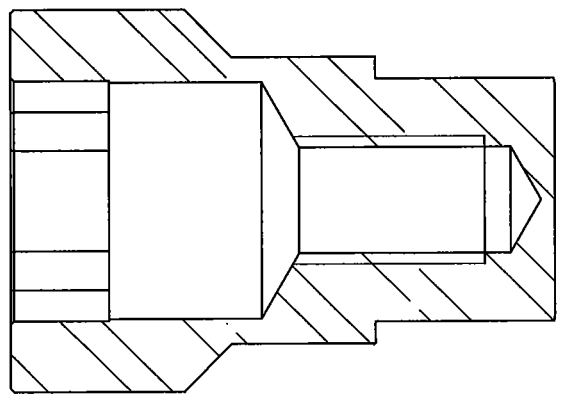
FIG. 7b a lab analog in section along the line of section E-E in accordance with the second embodiment.
Figure 7A:
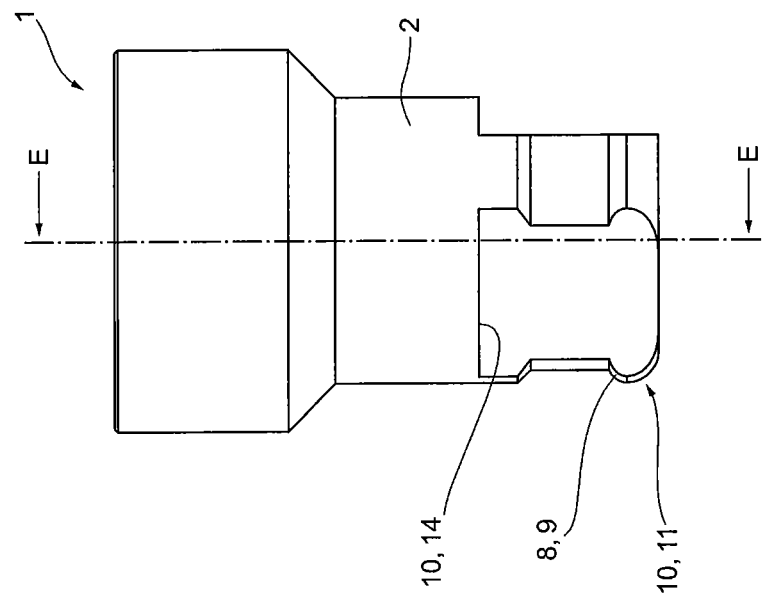
FIG. 7a a side view of a lab analog in accordance with a second embodiment with the line of section E-E.
Figure 8:
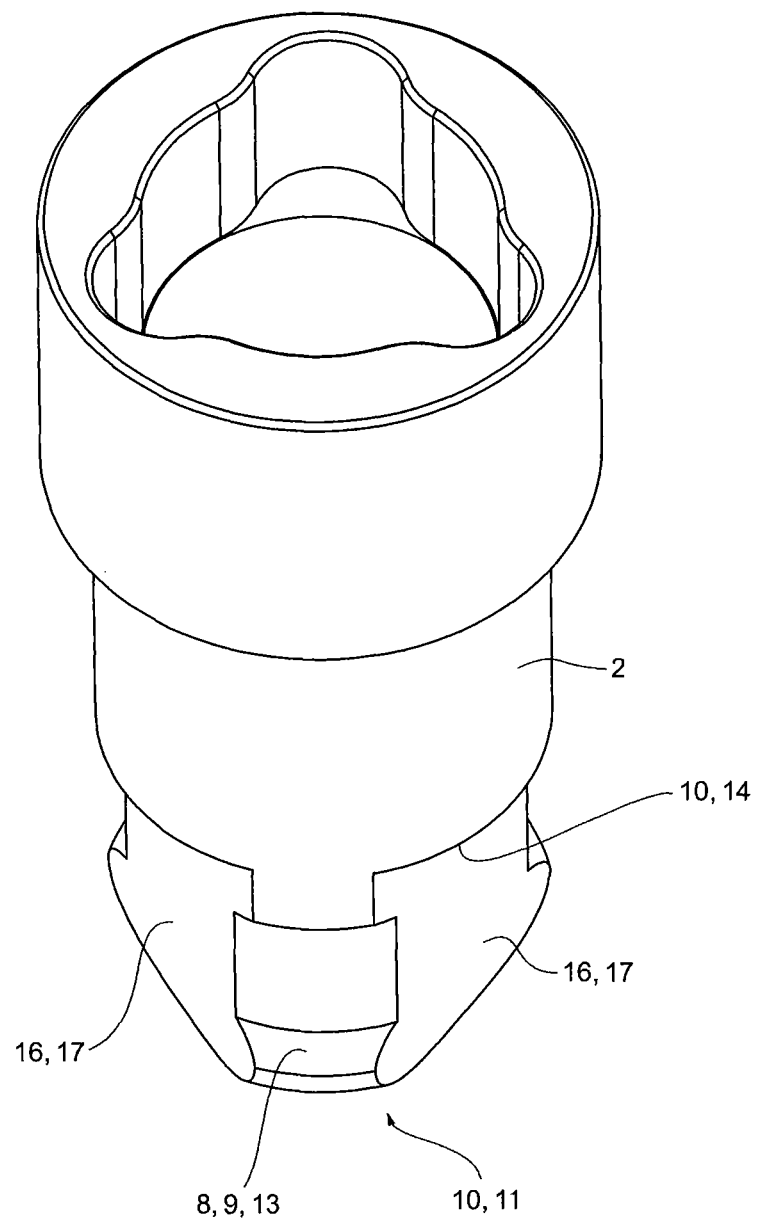
FIG. 8 the lab analog of FIG. 7a in a perspective view.

FIGS. 7a, 7b and 8 show a second embodiment of a lab analog 1. In contrast to the embodiment described above with respect to FIGS. 1a and 2, it is provided with three centering elements 8 disposed in the circumferential direction of the base body 2, which are formed as apical centering surfaces 9.

It is further distinguished by six restraining elements 10, three of which being beads 11 and three being steps 14. The beads 11 and the steps 14 are each uniformly disposed in the circumferential direction of the base body 2. Preferably, the beads 11 are offset by 60 degrees with respect to the steps 14 in the circumferential direction of the base body 2.

A further distinction is provided by the fixing elements 16, which are provided with three fixing surfaces 17 disposed in the circumferential direction of the base body 2. The fixing surfaces 17 are respectively parallel to the longitudinal axis of the base body 2 and confine the beads 11 on the circumferential side (in the circumferential direction). The normals to the surfaces of the fixing surfaces 17 are at an angle of 120 degrees with respect to each other.

Figure 9:
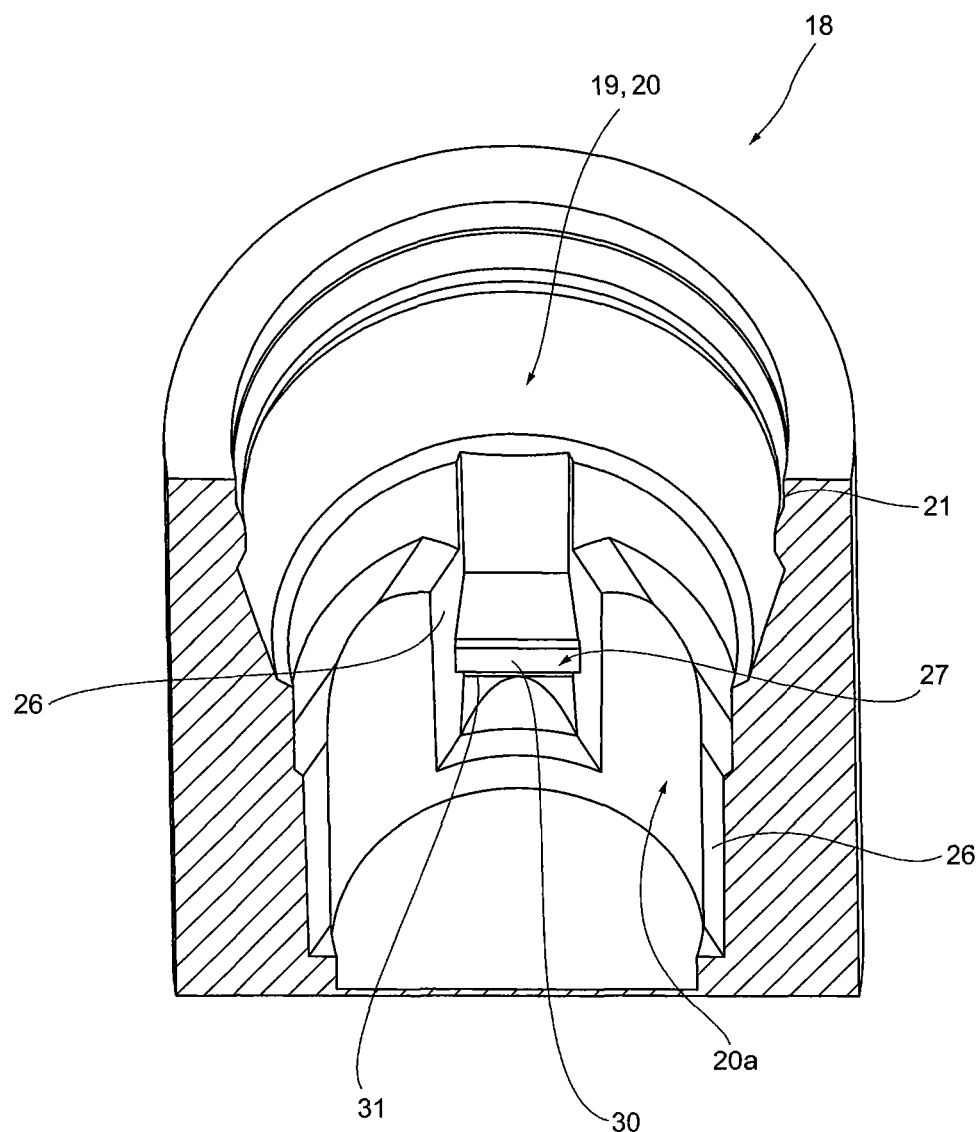
FIG. 9 a sectional view of a cavity in accordance with a second embodiment.

FIG. 9 shows a section of a second embodiment of a printed model 18 with a cavity 19. The cavity 19 is formed as a bore 20 with an inner wall 21. For the purposes of improved illustration, the outer boundary of the printed model 18 is shown as being round. It should be understood that FIG. 9 shows only a section of the printed model 18.

In contrast to the embodiment of FIG. 3, the bore 20 has six seating surfaces 26, with pairs thereof being disposed in one plane, preferably parallel to the longitudinal direction of the bore 20.

The projection 27 is also different. It has a flat front surface 30, the normal to the surface of which preferably being oriented perpendicular to the longitudinal axis of the bore 20. Optionally, the front surface 30 is arcuate. A lower side 31 of the projection 27 is configured as a flat surface in the circumferential direction of the bore 20 and as an arcuate surface in the radial direction of the bore 20, whereupon the arcuate surface profile follows the profile of the lateral surface 13 of the bead 11. The lower side 31 thus extends transversely to the longitudinal axis along a straight line and is arcuate in the radial direction of the bore 20. In other words, the lower side 31 is straight in one dimension and curved in another dimension.

A bead 11 of the lab analog 1 can engage behind the projection in the insertion direction in such a manner that the lateral surface 13 of the bead 11 (see FIG. 8) only seats in a narrow region on the underside 31 of the projection 27, for example along a straight line.

It should be understood that the embodiment of the projection 27 just described may also be used in the first embodiment of the printed model 18 in accordance with FIG. 3. Equally, it should be understood that the configuration of the projection 27 described in connection with the first embodiment in accordance with FIG. 3 may be employed in the second embodiment of the printed model 18 in accordance with FIG. 9.

In the context of the invention, it has been discovered that the friction upon insertion of the lab analog into the cavity is also determined by the size of the region in which the lateral surface 13 of the bead 11 seats on the underside of the projection 27. The smaller this region, the less friction is generated when the lab analog is inserted. If the lateral surface becomes seated at the underside 31 of the projection 27 along a line, then the friction is less than if nearly all of the lateral surface becomes seated on the projection 27.

Figure 10A:
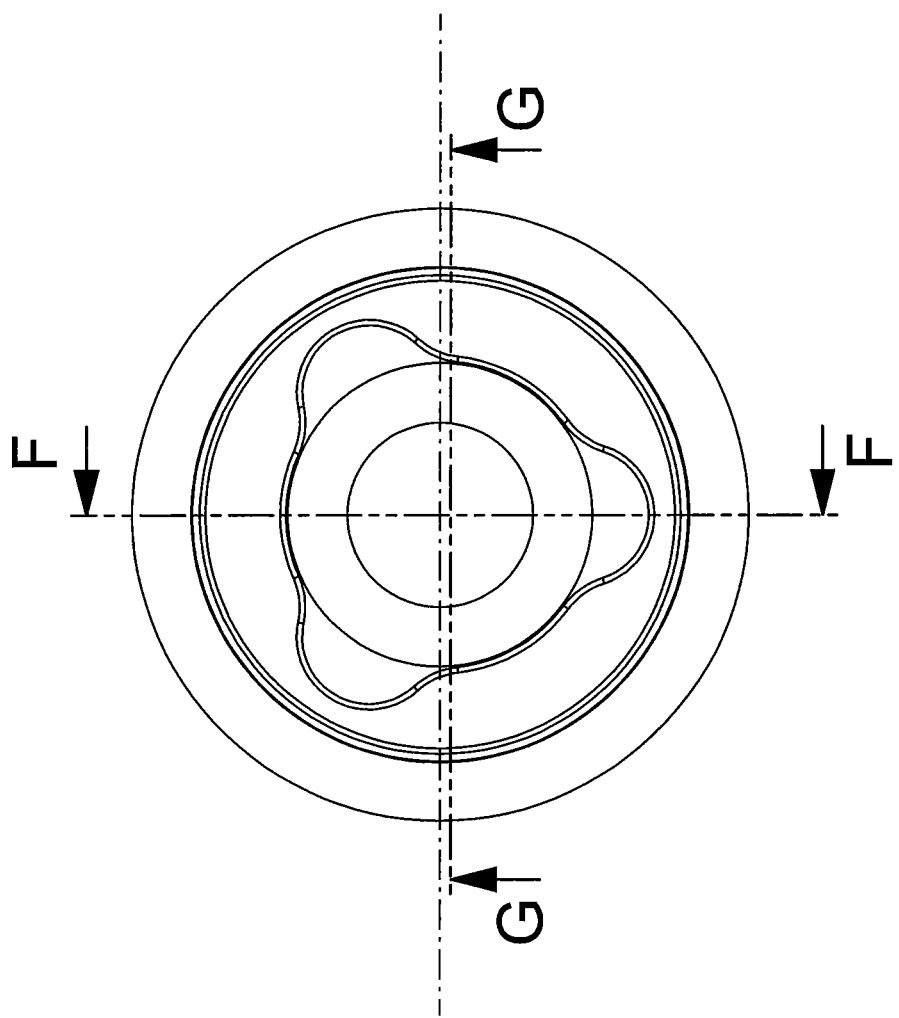
FIG. 10a a top view of a system in accordance with a second embodiment with two lines of section F-F and G-G.

FIGS. 10a to 10c show a second embodiment of the system 22 that comprises the lab analog 1 and the printed model 18 with the bore 20. The sectional representations of FIGS. 10b and 10c are rotated at 90° to each other; the plane of the section is off-center in FIG. 10c.

In contrast to the embodiment of the system 22 of FIGS. 4a to 6b, three centering elements 8 in the region of the apical end of the second centering section 5 now center the lab analog 1 in the bore 20. The centering elements 8 are configured as lateral surfaces 13 of the beads 11.

The second embodiment of the system 22 also differs in that three beads 11 engage behind the projections 27 of the bore 20, so that three steps 14 of the lab analog 1 become seated on three shoulders 25 of the bore 20. In this manner, the lab analog 1 is restrained in the bore 20 in the longitudinal direction.

A further difference is that now, instead of two fixing surfaces, three fixing surfaces 17 of the lab analog 1 are seated on six seating surfaces 26 of the bore 20. This ensures that the lab analog 1 is fixed against rotation in the bore 20. Any rotational forces that are generated here are distributed over six seating surfaces 26.

The invention claimed is:

1. Lab analog for insertion into a cavity of a printed model and for accommodating an abutment, comprising
    an essentially cylindrical base body that extends along a longitudinal axis,
    a first centering section for centering the lab analog in the cavity of the printed model, the first centering section adjoining the base body in a coronal direction,
    a second centering section for centering the lab analog in the cavity of the printed model, the second centering section adjoining the base body in an apical direction,
    restraining elements for restraining the lab analog in a longitudinal direction, and at least one fixing element to fix the lab analog against rotation,
    wherein the first centering section is provided with a centering surface and the second centering section is provided with at least one centering element which are both suitable for and configured to widen the cavity radially upon insertion of the lab analog,
    wherein the restraining elements include a first restraining element configured as a bead and a second restraining element configured as a step,
    wherein, when the lab analog has been inserted, the bead engages behind a projection in the cavity in the insertion direction in such a manner that the step becomes seated against a shoulder in the cavity,
    wherein the at least one fixing element is flat in configuration and rests against the printed model when the lab analog has been inserted, characterized in that wherein the bead has a lateral surface rounded in an insertion direction with a coronal region and an adjoining apical region,
wherein the lateral surface is asymmetrical in cross-section,
and
wherein the lateral surface has a different radius along the coronal region than along the adjoining apical region.

2. The lab analog according to claim 1, wherein the lateral surface has a smaller radius along the coronal region than along the adjoining apical region.

3. The lab analog according to claim 1, wherein the first centering section is provided with a centering chamber which adjoins a coronal centering surface in the coronal direction, wherein the first centering section has a larger diameter compared with the base body.

4. The lab analog according to claim 1, wherein the bead is disposed at an apical end of the second centering section and runs at least partially in a circumferential direction of the base body.

5. The lab analog according to claim 1, wherein the step is disposed at an apical end of the base body.

6. The lab analog according to claim 1, wherein the lab analog is provided with two mutually opposite centering elements or three centering elements disposed in a circumferential direction of the base body, and which are configured as apical centering surfaces.

7. The lab analog according to claim 1, wherein the restraining elements comprise four restraining elements, wherein two restraining elements are configured as beads and two restraining elements are configured as steps, wherein the beads and the steps are respectively disposed opposite each other.

8. The lab analog according to claim 1, wherein the restraining elements comprise four restraining elements, wherein two restraining elements are configured as beads and two restraining elements are configured as steps, wherein the beads and the steps are respectively disposed opposite each other, wherein the steps and the beads are offset by 90° to each other in a circumferential direction of the base body.

9. The lab analog according to claim 1, wherein the restraining elements comprise six restraining elements, wherein three restraining elements are configured as a bead and three restraining elements are configured as a step, wherein the beads and the steps are respectively uniformly distributed in a circumferential direction of the base body.

10. The lab analog according to claim 1, wherein the lab analog is provided with two or three centering elements, which are configured as apical centering surfaces, wherein the apical centering surfaces are configured as lateral surfaces of the beads.

11. The lab analog according to claim 1, wherein the fixing elements comprise two mutually parallel apical fixing surfaces or three apical fixing surfaces disposed in a circumferential direction of the base body, which are respectively disposed parallel to the longitudinal axis of the base body, and which confine the beads on a circumferential side.

12. A printed model with a cavity configured as a bore to accommodate a lab analog after insertion, wherein the contour of the printed model is designed in a printing process, the bore comprises an inner wall comprising:
an introduction section for introducing the lab analog, the introduction section extending apically from a coronal opening of the bore,
a radial tapering for centering the lab analog, the radial tapering being disposed in the introduction section,
a shoulder to limit a depth to which the lab analog is introduced, the shoulder adjoining the introduction section in a longitudinal direction of the bore,
at least one seating surface to fix the lab analog against rotation, the seating surface extending in an apical direction from the shoulder,
a projection, which tapers the bore radially and behind which a bead of the lab analog can engage in an introduction direction in such a manner that a step of the lab analog becomes seated at the shoulder, and
wherein the bore is configured such that upon inserting the lab analog into the bore, the bore is widened radially in the region of the projection by means of the bead of the lab analog.

13. The printed model according to claim 12, wherein the radial tapering 1s circumferentially disposed in the introduction section.

14. The printed model according to claim 12, comprising four, six or more than six seating surfaces at least some of which are parallel to each other and which extend up to a projection.

15. The printed model according to claim 12, wherein two seating surfaces are disposed in one plane parallel to the longitudinal direction of the bore.

16. A system comprising:
lab analog for insertion into a cavity of a printed model and for accommodating an abutment, comprising:
an essentially cylindrical base body that extends along a longitudinal
axis,
a first centering section for centering the lab analog in the cavity of the printed model, the first centering section adjoining the base body in a coronal direction,
a second centering section for centering the lab analog in the cavity of the printed model, the second centering section adjoining the base body in an apical direction,
restraining elements for restraining the lab analog in a longitudinal direction,
and at least one fixing element to fix the lab analog against rotation,
wherein the first centering section is provided with a centering surface and the second centering section is provided with at least one centering element which are both configured to widen the cavity radially upon insertion of the lab analog,
wherein the restraining elements include a first restraining element configured as a bead and a second restraining element configured as a step,
wherein, when the lab analog has been inserted, the bead engages behind a projection in the cavity in the insertion direction in such a manner that the step becomes seated against a shoulder in the cavity,
wherein the at least one fixing element is flat in configuration and rests against the printed model when the lab analog has been inserted,
wherein the bead has a lateral surface rounded in an insertion direction with a coronal region and an adjoining apical region,
wherein the lateral surface is asymmetrical in cross-section,
and
wherein the lateral surface has a different radius along the coronal region than along the adjoining apical region;
a printed model with a cavity configured as a bore to accommodate a lab analog wherein the bore comprises an inner wall comprising:

an introduction section for introducing the lab analog, the introduction section extending apically from a coronal opening of the bore, a radial tapering for centering the lab analog, the radial tapering being disposed in the introduction section, a shoulder to limit a depth to which the lab analog is introduced, the shoulder adjoining the introduction section in a longitudinal direction of the bore, at least one seating surface to fix the lab analog against rotation, the seating surface extending in an apical direction from the shoulder, and a projection, which tapers the bore radially and behind which a bead of the lab analog can engage in an introduction direction in such a manner that a step of the lab analog becomes seated at the shoulder.

17. A laboratory model with a cavity configured as a bore to accommodate a lab analog after insertion, wherein the bore comprises an inner wall comprising:

an introduction section for introducing the lab analog, the introduction section extending apically from a coronal opening of the bore, a radial tapering for centering the lab analog, the radial tapering being disposed in the introduction section, a shoulder to limit a depth to which the lab analog is introduced, the shoulder adjoining the introduction section in a longitudinal direction of the bore, at least one seating surface to fix the lab analog against rotation, the seating surface extending in an apical direction from the shoulder, and a projection, which tapers the bore radially and behind which a bead of the lab analog can engage in an introduction direction in such a manner that a step of the lab analog becomes seated at the shoulder, wherein the bore is configured such that upon inserting the lab analog into the bore, the bore is widened radially in the region of the projection by means of the bead of the lab analog.

* * * * *